United States Patent [19]

O'Brien

[11] Patent Number: 4,921,999

[45] Date of Patent: May 1, 1990

[54] METHOD FOR MAKING TERTIARY BUTYL ESTERS

[75] Inventor: Michael J. O'Brien, Albany, N.Y.

[73] Assignee: General Electric Company, Schenectady, N.Y.

[21] Appl. No.: 235,088

[22] Filed: Aug. 23, 1988

[51] Int. Cl.$^5$ .................. C07C 69/76; C07J 00/00
[52] U.S. Cl. .................. 560/52; 560/117; 560/116; 552/549
[58] Field of Search .................. 560/52, 117, 116; 260/397.1

[56] References Cited

FOREIGN PATENT DOCUMENTS 3206 7/1979 European Pat. Off. .

OTHER PUBLICATIONS

*Semiconductor International*, "Novolac Photoresists for Shorter Wavelengths", O'Brien et al., (1988), pp. 51–52.
McCloskey et al., *Organic Synthesis*, Coll. vol. IV, (1963), "Di-tert—Butyl Malonate", pp. 261–263.
Greene, *Alkyl Esters*, "Protective Groups in Organic Synthesis", (1981), pp. 168–169.
*J.C.S. Perkin II*, R. Roberts, "Kinetics and Mechanism of Addition of Acids to Olefins, Part I, Addition of Acetic Acid to Cyclic and Strained Bicyclic Olefins Catalyzed by Trifluoromethanesulphonic Acid", pp. 1183–1190.
M. J. O'Brien et al., Proceedings of SPIE (1988); Paper 920–06.
*J. Org. Chem.*, Holcombe et al., "A New and Specific Method for the Protection of Phenols as the Corresponding tert-Butyl Ethers", (1986), pp. 111–113.

*Primary Examiner*—Paul J. Killos
*Attorney, Agent, or Firm*—William A. Teoli; James C. Davis, Jr.; William H. Pittman

[57] ABSTRACT

A method is provided for making tertiary butyl esters by effecting reaction between an organic carboxylic acid and isobutylene in the presence of an effective amount of trifluoromethane sulfonic acid at temperatures below about $-7°$ C. Tertiary butyl esters are useful as dissolution inhibitors for novolak resins.

4 Claims, No Drawings

METHOD FOR MAKING TERTIARY BUTYL ESTERS

BACKGROUND OF THE INVENTION

As taught by M. J. O'Brien et al., Semiconductor International (May 1988) pages 51-52, certain tertiary-butyl esters, such as t-butyl naphthalene carboxylate are useful as dissolution inhibitors for deep-UV (250-300 novolak) novolak base photoresists. Mid-UV photoresists (300-350 nanometers) combining chemical amplification and dissolution inhibition also are made possible as a result of the use of t-butyl ester dissolution inhibitors as taught by M. J. O'Brien and J. V. Crivello, "Proceedings of SPIE" (1988) 920, 42.

J. L. Holcombe and T. Livinghouse, in the Journal of Organic Chemistry 51 (1986) pages 111-113, indicate that the synthesis of t-butyl esters can be achieved by effecting reaction between isobutylene and an appropriate carboxylic acid. However, the reaction is effected at high pressure. A procedure for synthesizing t-butyl esters employing elevated pressure and sulfuric acid is also outlined by L. F. Fieser and M. Fieser in "Reagents for Organic Synthesis", Wiley, New York, Vol. 1 (1967) page 522.

A high pressure synthesis is also used to prepare the corresponding ethyl- or isopropyl-esters of carboxylic acids taught by M. Gruffaz and O. Micaelli, Chemical Abstracts 92: 22064a. The ethyl and isopropyl carboxylic acid esters are prepared by utilizing a trifluoromethane sulfonic acid catalyst.

Addition of acetic acid to cyclic and strained bicyclic olefins catalyzed by trifluoromethane sulfonic acid is taught by R. M. G. Roberts, J. C. S. Perkin II (1976) pages 1183-1190.

Although tertiary butylesters, useful as dissolution inhibitors for novolak photoresists can be made by employing techniques requiring the use of sulfuric acid and isobutylene at elevated pressures, it would be desirable to synthesize such tertiary butyl esters by effecting reaction between an organic carboxylic acid, and isobutylene at atmospheric pressure for a period of about one hour or less.

The present invention is based on the discovery that a highly efficient method of adding isobutylene to carboxylic acid at atmospheric pressure is provided to produce a variety of tertiary butylesters by contacting the carboxylic acid with isobutylene at a temperature of about $-7°$ C. or less in the presence of an effective amount of trifluoromethane sulfonic acid.

STATEMENT OF THE INVENTION

There is provided by the present invention, a method for making tertiary butylesters, which comprises (1) effecting reaction at a temperature of less than about $-7°$ C., between organic carboxylic acid and isobutylene, in the presence of a substantially inert organic solvent, an effective amount of trifluoromethane sulfonic acid, and (2) adding an acid acceptor to the mixture of (1) and thereafter effecting the removal of the organic solvent.

Some of the carboxylic acids which can be used in the practice of the present invention to make the tertiary butylesters are compounds included within the following formula

where R is $C_{(1-20)}$ organic radical selected from alkyl radicals, cycloalkyl radicals, alkylene radicals, aryl radicals and arylene radicals, and halogenated derivatives thereof, a is an integer having a value of 1 or 2, and when a is 1, R is monovalent and when a is 2, R is divalent.

Included within the preferred carboxylic acids are compounds such as triformylcholic acid, adamantane carboxylic acid, malonic acid and o-benzoylbenzoic acid.

Substantially inert organic solvents which can be used in the practice of the present invention are, for example, dichloromethane, 1,2-dichloroethane and chloroform.

Acid acceptors which can be used in the practice of the invention are, for example, alkali metal hydroxides, such as sodium hydroxide and tertiary amines, such as triethylamine and pyridine.

In the practice of the present invention, reaction is effected between the carboxylic acid in the form of an organic solvent solution at temperatures in the range of from about $-7°$ C. to $-70°$ C. and preferably $-10°$ C. to $-30°$ C. Contact between the carboxylic acid solution and isobutylene can be achieved under normal atmospheric pressure. The addition of an effective amount of the trifluoromethane sulfonic acid or "triflic acid" can be added with stirring. An effective amount of triflic acid is from 1% to 10% by weight, based on the weight of the reaction mixture. The acid acceptor is used in at least a stoichiometric amount with respect to the triflic acid, followed by allowing the mixture to warm to room temperature. Recovery of the tertiary butylester can then be effected by concentrating the mixture under reduced pressure. The resulting crude product is then recrystallized in a suitable solvent or distilled.

In order that those skilled in the art will be better able to practice the present invention, the following examples are given by way of illustration and not by way of limitation. All parts are by weight unless otherwise indicated.

EXAMPLE 1

There was added 36 ml of isobutylene to a solution of 35.78 grams (72.7 mmol) of triformylcholic acid dissolved in 90 ml of dichloromethane which was cooled to $-30°$ C. There was then added to the resulting mixture, 0.5 ml (5.6 mmol) of triflic acid, along with stirring the resulting mixture for one hour while it was maintained between $-20°$ C. and $-30°$ C. There was then added 2.5 ml of triethylamine and the reaction mixture was warmed to room temperature. The mixture was then concentrated under reduced pressure and the residue was dissolved in ether and washed with 5% HCl, three times with water, and then concentrated sodium chloride solution. The residue was then dried over anhydrous sodium sulfate, followed by concentration under reduced pressure, and recrystallization from hexane/ethyl acetate mixture. There was obtained 32.58 grams of product (82% yield) in the form of a white powder. Based on method of preparation, the product was t-butyl triformylcholate. The identity of the product was further confirmed by its NMR spectra and melting point of 136°-137° C.

A positive photoresist is prepared using 20% by weight of the above t-butyl triformylcholate, 75% by weight of novolak resin and 5% by weight of diphenyliodonium hexafluoroantimonate. The photoresist is spin-coated and patterned onto the surface of a silicon wafer as a 20% solids solution in 1-methoxy-2-propyl acetate solvent. It is found that the t-butyl triformylcholate performs satisfactorily as a dissolution inhibitor.

EXAMPLE 2

There was added 15 ml of isobutylene, followed by 0.4 ml (4.5 mmol) of triflic acid to a solution in 40 ml of dichloromethane cooled to −20° C. of 10.0 grams (55.5 mmol) of 1-adamantane carboxylic acid. The resulting solution was stirred for one hour at this temperature after which 2.5 ml of triethylamine was added with stirring and the mixture was allowed to warm up to room temperature. Heating under reduced pressure provide a white crude solid product in nearly quantitative yield. Gas chromatographic analysis indicated that the material was about 94% pure. Recrystallization from n-hexane provided 9.67 grams (74%) of pure material. Based on NMR analysis and its melting point of 47°–48° C., the product was identified as t-butyl adamantane-1-carboxylate.

EXAMPLE 3

There was added 14 ml of isobutylene, followed by 0.3 ml (23.4 mmol) of triflic acid to a solution of 10 grams (72.7 mmol) of o-benzoyl benzoic acid dissolved in 40 ml of dichloromethane, cooled to −20° C. Within seconds after the addition of the triflic acid, the solution which was initially cloudy became clear. The solution was then stirred for 30 minutes at −15° C. to −20° C. and 1 ml (7.2 mmol) of triethylamine was added. The reaction mixture was allowed to warm to room temperature. Concentration under reduced pressure provided a solid residue which was recrystallized twice from n-hexane. There was obtained 10.4 grams (84% yield) of product with a melting point of 67°–69° C. Based on method of preparation and $H^1$ NMR data, the product was t-butyl o-benzoylbenzoate.

Although the above examples are directed to only a few of the very many variables which can be utilized in the practice of the present invention, it should be understood that the present invention is directed to a method for making a much broader variety of t-butyl esters as set forth in the description proceeding these examples.

What is claimed and sought to be protected by Letters Patent of the U.S. is as follows:

1. A method for making tertiary butyl-esters, which comprises effecting reaction at atmospheric pressure and at a temperature of less than about −7° C., between
   (1) an organic carboxylic acid and isobutylene, in the presence of a substantially inert organic solvent and an effective amount of trifluoromethane sulfonic acid and
   (2) adding an acid acceptor to the mixture of (1) and thereafter effecting the removal of organic solvent.

2. A method in accordance with claim 1, wherein the carboxylic acid is triformylcholic acid.

3. A method in accordance with claim 1, wherein the carboxylic acid is 1-adamantane carboxylic acid.

4. A method in accordance with claim 1, wherein the carboxylic acid is o-benzoylbenzoic acid.

* * * * *